United States Patent
Nagai et al.

(10) Patent No.: US 12,318,467 B2
(45) Date of Patent: Jun. 3, 2025

(54) COSMETIC

(71) Applicant: Shiseido Company, Ltd., Tokyo (JP)

(72) Inventors: Kouichi Nagai, Tokyo (JP); Takashi Matsui, Tokyo (JP)

(73) Assignee: Shiseido Company, Ltd., Tokyo (JP)

( * ) Notice: Subject to any disclaimer, the term of this patent is extended or adjusted under 35 U.S.C. 154(b) by 568 days.

(21) Appl. No.: 17/761,455

(22) PCT Filed: Sep. 15, 2020

(86) PCT No.: PCT/JP2020/034946
§ 371 (c)(1),
(2) Date: Mar. 17, 2022

(87) PCT Pub. No.: WO2021/060079
PCT Pub. Date: Apr. 1, 2021

(65) Prior Publication Data
US 2022/0362129 A1 Nov. 17, 2022

(30) Foreign Application Priority Data

Sep. 27, 2019 (JP) ................. 2019-176896
Aug. 28, 2020 (JP) ................. 2020-144059

(51) Int. Cl.
*A61K 8/73* (2006.01)
*A61G 17/04* (2006.01)
*A61K 8/06* (2006.01)
*A61K 8/92* (2006.01)
*A61Q 17/04* (2006.01)

(52) U.S. Cl.
CPC .............. *A61K 8/732* (2013.01); *A61G 17/04* (2013.01); *A61K 8/064* (2013.01); *A61K 8/92* (2013.01)

(58) Field of Classification Search
CPC .......... A61K 8/732; A61K 8/064; A61K 8/92; A61Q 17/04
See application file for complete search history.

(56) References Cited

U.S. PATENT DOCUMENTS

| | | | |
|---|---|---|---|
| 4,894,222 | A | 1/1990 | Matravers |
| 6,599,512 | B1 | 7/2003 | Burnier |
| 2005/0058678 | A1 | 3/2005 | Ricard et al. |
| 2005/0069511 | A1 | 3/2005 | Magnet et al. |
| 2015/0196463 | A1 | 7/2015 | Jansen et al. |
| 2015/0196465 | A1 | 7/2015 | Jansen et al. |
| 2016/0374933 | A1 | 12/2016 | Tanner et al. |

FOREIGN PATENT DOCUMENTS

| | | |
|---|---|---|
| GB | 1 404 583 | 9/1978 |
| JP | 03-112921 | 5/1991 |
| JP | 10-114621 A | 5/1998 |
| JP | 11-079938 A | 3/1999 |
| JP | 11-092329 A | 4/1999 |
| JP | 11-246379 A | 9/1999 |
| JP | 2000-219609 A | 8/2000 |
| JP | 2001-294512 A | 10/2001 |
| JP | 2003-503316 A | 1/2003 |
| JP | 2003-095908 A | 4/2003 |
| JP | 2003-112921 A | 4/2003 |
| JP | 2004-529957 | 9/2004 |
| JP | 2005-053909 | 3/2005 |
| JP | 2007-217361 A | 8/2007 |
| JP | 2011-098929 A | 5/2011 |
| JP | 2013-199443 A | 10/2013 |
| JP | 2015-117209 A | 6/2015 |

OTHER PUBLICATIONS

Japan Institute of Invention and Innovation, Public Technical Journal No. 2003-500995, Feb. 27, 2003, Matsumoto Trading Co., Ltd., with English translation.
J-Stage Home page, Applied Glycoscience, The Japanese society of Applied Glycoscience, 2012, 2(2): 150, with English machine translation.
Japanese Cosmetic Labeling Name Dictionary (JCLD), Japanese Cosmetic Ingredient Labeling Dictionary, 3rd edition, Yakuji Nipposha, 2013, p. 252, with English machine translation.

*Primary Examiner* — Shirley V Gembeh
(74) *Attorney, Agent, or Firm* — Foley & Lardner LLP

(57) ABSTRACT

Providing a cosmetic having a smooth after-feel even if the cosmetic contains a high proportion of oil. A cosmetic includes (A) a starch powder, and as oils, (B) a polar oil and (C) a volatile oil. The ratio of (C) the volatile oil to (B) the polar oil being 0.5 or higher.

12 Claims, No Drawings

COSMETIC

CROSS-REFERENCE TO RELATED APPLICATIONS

This application is a National Phase Entry of PCT International Application No. PCT/JP2020/034946 filed on Sep. 15, 2020, which claims priority under 35 U.S.C. § 119(a) to Japanese Patent Application No. 2019-176896 filed on Sep. 27, 2019 and Japanese Patent Application No. 2020-144059 filed on Aug. 28, 2020.

TECHNICAL FIELD

The present disclosure relates to a cosmetic, specifically a cosmetic containing a starch powder.

BACKGROUND ART

In general, cosmetic products include various types of powders for purposes such as skin tone improvement, ultraviolet light (UV) protection, and sweat and sebum adsorption. For example, PCT Japanese Publication No. 2003-503316 discloses a solid aqueous gel containing a combination of a hydrophilic gelling agent and a starch or a derivative thereof, and PCT Japanese Publication No. 2004-529957 discloses a cosmetic composition containing a carboxylic acid ester and a starch. According to the above documents, starch is added for purposes such as gelation.

Meanwhile, Japanese Unexamined Patent Publication No. H11(1999)-246379 discloses a sunscreen cosmetic containing ethanol, a starch, and a UV scattering agent or a UV absorber, and providing for example a pleasant cooling or smooth afterfeel when the sunscreen cosmetic is applied onto the skin.

SUMMARY

Technical Problem

The sunscreen cosmetic disclosed in Japanese Unexamined Patent Publication No. H11(1999)-246379 exhibits a smooth feel effect attributable to a starch when being applied onto the skin. However, due to a high mix proportion of ethanol, it is impossible to mix in a high amount of an oily UV absorber. In order to mix in a high amount of a UV absorber, a high amount of oil must be inevitably mixed in. In this case, however, it is difficult to mix in a starch, which is hydrophilic. The present inventors have earnestly studied to find that a smooth feel attributable to a starch can be obtained by mixing oils in a specific proportion even though a high proportion of the oils are mixed in.

The present disclosure was completed in view of the above circumstances, and the present disclosure provides a cosmetic having a smooth afterfeel even though a high proportion of oil is mixed in.

Cosmetics according to the present disclosure contain (A) a starch powder, and as oils,
  (B) a polar oil, and
  (C) a volatile oil,
in which the ratio of (C) the volatile oil to (B) the polar oil is 0.5 or higher.

(A) the starch powder is preferably dispersed in the oils.

Cosmetics according to the present disclosure preferably additionally contain (D) an oil phase thickener.

Cosmetics according to the present disclosure may further contain (E) a non-volatile hydrocarbon oil or a non-volatile silicone oil, and in this case, the ratio of (E) the non-volatile hydrocarbon oil or the non-volatile silicone oil to (B) the polar oil is preferably 0.5 or lower.

(B) the polar oil may contain a UV absorber.

Cosmetics according to the present disclosure may be water-in-oil type emulsified cosmetics.

Cosmetics according to the present disclosure may be oily cosmetics.

Since cosmetics according to the present disclosure contain (A) a starch powder, and
as oils,
  (B) a polar oil, and
  (C) a volatile oil,
in which the ratio of (C) the volatile oil to (B) the polar oil is 0.5 or higher, a smooth afterfeel can be obtained by the cosmetics even though a high proportion of the oils are mixed in.

DESCRIPTION OF EMBODIMENTS

Cosmetics according to the present disclosure are described in detail below.

A cosmetic according to the present disclosure contains (A) a starch powder, and
as oils,
  (B) a polar oil, and
  (C) a volatile oil,
in which the ratio of (C) the volatile oil to (B) the polar oil is 0.5 or higher.

Each ingredient is closely described below. Each ingredient may be simply referred to for example as (A) ingredient or (B) ingredient. In the present specification, PEG, PPG, PBG, EO, PO, POE, POP, and VP are abbreviations for polyethylene glycol, polypropylene glycol, polybutylene glycol, ethylene oxide, propylene oxide, polyoxyethylene, polyoxypropylene, and vinylpyrrolidone, respectively.

(A) Starch Powder (A) The starch is not particularly limited as long as the starch is ordinarily used in cosmetics, pharmaceuticals, and food products, and is exemplified by, but is not limited to, potatostarch, cornstarch, dextrin, or chemically modified materials having the backbone structures thereof.

Examples of the above chemically modified materials each having the backbone structure for example of potatostarch, cornstarch, or dextrin are hydroxypropyl starch, sodium cornstarch octenylsuccinate, aluminum cornstarch octenylsuccinate, triethanolamine cornstarch octenylsuccinate, sodium starch octenylsuccinate, and triethanolamine starch octenylsuccinate. However, functional groups for chemical modification are not limited thereto.

As (A) ingredient, one type may be used alone or 2 or more types may be used simultaneously.

The mix proportion of (A) ingredient is preferably 0.1 to 10% by weight and more preferably 0.5 to 5% by weight of the total amount of the cosmetic. When the mix proportion is 0.1% by weight or greater, a smooth feel can be effectively imparted to cosmetics, and when the mix proportion is 10% by weight or less, (A) ingredient can be mixed in stably.

(A) ingredient is preferably dispersed in oils. A starch powder is hydrophilic. However, since cosmetics according to the present disclosure have the ratio of (C) the volatile oil to (B) the polar oil of 0.5 or higher, (A) ingredient can be dispersed in oils, and due to (A) ingredient being dispersed in oils, a stronger smooth feel is perceptible.

(B) Polar Oil

The oils include (B) the polar oil. (B) ingredient is not particularly limited as long as being ordinarily used in cosmetics, pharmaceuticals, and food products. The IOB value is not particularly limited and is preferably 0.05 to 0.80.

The IOB value is an abbreviation for Inorganic/Organic Balance (inorganicity/organicity ratio), which represents a ratio of an inorganic value to an organic value and is an indicator showing a degree of polarity of an organic compound. The IOB value is specifically represented by IOB value=inorganic value/organic value.

Here, each of the "inorganic value" and "organic value" is determined in accordance with atoms and functional groups, and in a molecule, for example, one carbon atom is determined to have an "organic value" of 20 and one hydroxy group is determined to have an "inorganic value" of 100. By adding up the "inorganic value" and "organic value" of all the atoms and functional groups in an organic compound, the IOB value of the organic compound can be calculated (see for example, Fujita, "Journal of Japanese Chemistry", Vol. 11, No. 10, pages 719 to 725, 1957).

Typical examples of the polar oil are ester oils and UV absorbers.

Specific examples of the ester oils are tripropyleneglycol dineopentanoate, isononyl isononanoate, isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, acetylated lanolin, isocetyl stearate, isocetyl isostearate, cholesteryl hydroxy 12-stearate, cetyl ethylhexanoate, ethyleneglycol di-2-ethylhexanoate, dipentaerythritol fatty acid esters, n-alkylglycol monoisostearate, neopentylglycol dicaprate, diisostearyl malate, glycerin di-2-heptylundecanoate, trimethylolpropane tri-2-ethylhexanoate, trimethylolpropane triisostearate, pentaerythrityl tetra-2-ethylhexanoate, triethylhexanoin (glycerin tri-2-ethylhexanoate), glycerin trioctanoate, glycerin triisopalmitate, trimethylolpropane triisostearate, cetyl 2-ethyl hexanoate, 2-ethylhexyl palmitate, glycerin trimyristate, glyceride tri-2-heptyl undecanoate, fatty acid methyl esters from castor oil, oleyl oleate, acetoglyceride, 2-heptyl undecyl palmitate, diisobutyl adipate, 2-octyldodecyl N-lauroyl-L-glutamate, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, and triethyl citrate.

The UV absorbers are exemplified by, but are not particularly limited to, a broad range of oily UV absorbers having high polarity that are generally used in cosmetics. Examples thereof are benzoic acid derivatives, salicylic acid derivatives, cinnamic acid derivatives, dibenzoylmethane derivatives, β,β-diphenylacrylate derivatives, benzophenone derivatives, benzylidene camphor derivatives, phenylbenzimidazole derivatives, triazine derivatives, phenylbenzotriazole derivatives, anthranyl derivatives, imidazoline derivatives, benzalmalonate derivatives, and 4,4-diarylbutadiene derivatives. The following are specific examples and product names of the UV absorbers, which are not limited thereto.

Examples of the benzoic acid derivatives include para-aminobenzoic acid (PABA) ethyl, ethyl-dihydroxypropyl PABA, ethylhexyl-dimethyl PABA (such as "ESCALOL 507" produced by ISP), glyceryl PABA, PEG-25-PABA (such as "Uvinul P25", produced by BASF), and diethylamino hydroxybenzoyl hexyl benzoate (such as "Uvinul A Plus").

Examples of the salicylic acid derivatives include homosalate ("Eusolex HMS", produced by Rona/EM Industries), ethylhexyl salicylate (such as "NeoHeliopan OS", produced by Haarman and Reimer), dipropyleneglycol salicylate (such as "Dipsal", produced by Scher), and TEA salicylate (such as "NeoHeliopan TS", produced by Haarman and Reimer).

Examples of the cinnamic acid derivatives include octyl methoxycinnamate or ethylhexyl methoxycinnamate (such as "Parsol MCX", produced by Hoffmann-La Roche), isopropyl methoxycinnamate, isoamyl methoxycinnamate (such as "NeoHeliopan E1000", produced by Haarman and Reimer), cinoxate, DEA methoxycinnamate, diisopropyl methylcinnamate, glyceryl-ethylhexanoate-dimethoxy cinnamate, and di-(2-ethylhexyl)-4'-methoxybenzal malonate.

Examples of the dibenzoylmethane derivatives include 4-tert-butyl-4'-methoxydibenzoylmethane (such as "Parsol 1789").

Examples of the β,β-diphenylacrylate derivatives include octocrylene (such as "Uvinul N539", produced by BASF).

Examples of the benzophenone derivatives include benzophenone-1 (such as "Uvinul 400", produced by BASF), benzophenone-2 (such as "Uvinul D50", produced by BASF), benzophenone-3 or oxybenzone (such as "Uvinul M40", produced by BASF), benzophenone-4 (such as "Uvinul M540", produced by BASF), benzophenone-5, benzophenone-6 (such as "Helisorb 11", produced by Norquay), benzophenone-8 (such as "Spectra-Sorb UV-24", produced by American Cyanamid), benzophenone-9 (such as "Uvinul DS-49", produced by BASF), and benzophenone-12.

Examples of the benzylidene camphor derivatives include 3-benzylidene camphor (such as "Mexoryl SD", produced by Chimex), 4-methylbenzylidene camphor, benzylidene camphor sulfonic acid (such as "Mexoryl SL", produced by Chimex), camphor benzalkonium methosulfate (such as "Mexoryl SO", produced by Chimex), terephthalylidene dicamphor sulfonic acid (such as "Mexoryl SX", produced by Chimex), and polyacrylamide methylbenzylidene camphor (such as "Mexoryl SW", produced by Chimex).

Examples of the phenylbenzimidazole derivatives include phenylbenzimidazole sulfonic acid (such as "Eusolex 232", produced by Merck), disodium phenyl dibenzimidazole tetrasulfonate (such as "NeoHeliopan AP", produced by Haarman and Reimer).

Examples of the triazine derivatives include anisotriazine (such as "Tinosorb S", produced by Ciba Specialty Chemicals), ethylhexyl triazone (such as "Uvinul T150" produced by BASF), diethylhexyl butamido triazone (such as "Uvasorb HEB", produced by 3V Sigma), and 2,4,6-tris(diisobutyl-4'-aminobenzalmalonate)-s-triazine.

Examples of the phenylbenzotriazole derivatives include drometrizole trisiloxane (such as "Silatrizole" produced by Rhodia Chimie), and methylene bis(benzotriazolyl tetramethylbutylphenol) (such as "Tinosorb M", produced by Ciba Specialty Chemicals).

Examples of the anthranil derivatives include menthyl anthranilate (such as "NeoHeliopan MA", produced by Haarman and Reimer).

Examples of the imidazoline derivatives include ethylhexyl dimethoxybenzylidene dioxoimidazoline propionate.

Examples of the benzalmalonate derivatives include a polyorganosiloxane having a benzalmalonate functional group (such as polysilicone-15, "Parsol SLX", produced by DSM Nutrition Japan).

Examples of the 4,4-diarylbutadiene derivatives include 1,1-dicarboxy(2,2'-dimethylpropyl)-4,4-diphenylbutadiene.

As (B) ingredient, one type may be used alone or 2 or more types may be used simultaneously.

The mix proportion of the polar oil can be appropriately adjusted within the ratio of the polar oil to (C) the volatile oil described below in accordance with the properties and applications of a cosmetic, and is preferably 1 to 40% by weight, preferably 3 to 35% by weight, and more preferably 5 to 30% by weight, relative to the total amount of the cosmetic. The mix proportion of a UV absorber contained in the polar oil is 40% by weight or greater, preferably 50% by weight or greater, and more preferably 60% by weight or greater of the polar oil. The entirety of the polar oil may be a UV absorber. Due to the amount of the polar oil of 1% by weight or greater, a stronger smooth feel derived from a starch powder is perceptible and due to the amount being 40% by weight or less, greasiness can be more suppressed.

(C) Volatile Oil

The oils include (C) a volatile oil. (C) ingredient is exemplified by a hydrocarbon oil having a relatively low molecular weight, a linear silicone having a relatively low molecular weight, and a cyclic silicone having a relatively low molecular weight, and light liquid isoparaffin, isododecane, isohexadecane, volatile dimethylpolysiloxane (volatile dimethicone), or cyclic polysiloxane is particularly preferred. Specific examples include octamethylcyclotetra siloxane, decamethylcyclopenta siloxane, dodecamethylcyclohexa siloxane, and hexadecamethyl cyclohepta siloxane.

As (C) ingredient, one type may be used alone or 2 or more types may be used simultaneously.

The mix proportion of the volatile oil can be appropriately adjusted within the range of the ratio of the volatile oil to the above (B) ingredient in accordance with the properties and applications of a cosmetic and is preferably 5 to 60% by weight and more preferably 10 to 40% by weight relative to the entire amount of the cosmetic. When the mix proportion of the volatile oil is 5% by weight or greater, favorable application properties can be obtained. In addition, when the mix proportion is 60% by weight or less, appropriate viscosity can be maintained.

The ratio of (C) ingredient to (B) ingredient ((C) ingredient/(B) ingredient) is 0.5 or higher, more preferably 0.55 or higher, and still more preferably 0.6 or higher and 1.5 or lower. When the ratio of (C) ingredient/(B) ingredient is 0.5 or higher, a smooth afterfeel can be obtained while stable powder mixing in can be performed, even when the oil proportion is high. In addition, when the ratio of (C) ingredient/(B) ingredient is 1.5 or lower, more appropriate viscosity can be maintained.

(D) Oil Phase Thickener

Cosmetics according to the present disclosure preferably additionally contain (D) an oil phase thickener. Due to an oil phase thickener contained, the viscosity of cosmetics can be easily adjusted. Preferred examples of (D) ingredient include dextrin fatty acid esters, sucrose fatty acid esters, fatty acids or salts thereof, hardened vegetable oil or solid or semisolid vegetable oil, glyceryl fatty acid esters, and amino acid-based gelling agents.

As the dextrin fatty acid esters, esters of dextrin or reduced dextrin and higher fatty acids that are generally used in cosmetics may be used without particular restriction. Dextrin or reduced dextrin having an average sugar polymerization degree of 3 to 100 is preferably used. In addition, as fatty acids constituting the dextrin fatty acid esters, $C_8$ to $C_{22}$ saturated fatty acids are preferably used. Specific examples thereof include dextrin palmitate, dextrin oleate, dextrin stearate, dextrin myristate, and (palmitic acid/2-ethylhexanoic acid) dextrin.

As the sucrose fatty acid esters, those containing linear or branched and saturated or unsaturated fatty acids having 12 to 22 carbon atoms may be preferably used. Specific examples include sucrose caprylate, sucrose caprate, sucrose laurate, sucrose myristate, sucrose palmitate, sucrose stearate, sucrose oleate, and sucrose erucate.

As the fatty acids, those being solid at room temperature may be used, and examples thereof include myristic acid, palmitic acid, stearic acid, and behenic acid. Examples of salts of fatty acids include calcium salts, magnesium salts, and aluminum salts thereof.

Examples of the hardened vegetable oil include hardened palm kernel oil, hydrogenated castor oil, hydrogenated peanuts oil, hydrogenated rapeseed oil, hydrogenated palm oil, hydrogenated *camellia* oil, hydrogenated soybean oil, hydrogenated olive oil, hydrogenated macadamia seed oil, hydrogenated sunflower oil, hydrogenated wheat germ oil, hydrogenated rice germ oil, hydrogenated rice bran oil, hydrogenated cotton seed oil, and hydrogenated avocado oil.

Similarly to the hardened vegetable oil, vegetable oil being solid or semisolid at room temperature may also be used. Here, hardened oil means oil being solid at a temperature of 25° C., and semisolid oil means oil in which half the amount of the oil is solid at a temperature of 25° C. More specifically, oils having a melting point within a range of 44° C. to 90° C., a viscosity measured at a temperature of 25° C. with a Brookfield viscometer of 5,000 mPa·s or greater and further of 10,000 mPa·s or greater are preferred. Examples of vegetable oils being solid or semisolid at room temperature include cacao butter, coconut oil, palm oil, palm kernel oil, Japan tallow, and shea butter.

As the glyceryl fatty acid esters, esterification reaction products obtained by reacting glycerin, $C_{18}$ to $C_{28}$ dibasic acids, and $C_8$ to $C_{28}$ fatty acids (excluding dibasic acids), being generally used in cosmetics may be used without particular restriction. Specific examples include (behenic acid/isostearic acid/eicosanedioic acid) glyceryl, (behenic acid/eicosanedioic acid) glyceryl, and (behenic acid/eicosanedioic acid) polyglyceryl-10.

Examples of the amino acid-based gelling agents include dibutyl lauroyl glutamide, dibutyl ethylhexanoyl glutamide, polyamide-8, polyamide-3, and N-lauroyl-L-glutamic acid dibutylamide.

As (D) ingredient, one type may be used alone or 2 or more types may be used simultaneously.

The mix proportion of (D) ingredient is, relative to the entire amount of a cosmetic, preferably 0.1 to 15% by weight, more preferably 0.3 to 10% by weight, and still more preferably 0.5 to 8% by weight. When the mix proportion of (D) ingredient is 0.1% by weight or greater, appropriate viscosity can be imparted and the ease of application onto the skin can be further improved. When the mix proportion is 15% by weight or less, more favorable usability, for example appropriate spreadability on the skin, can be achieved.

(E) Non-Volatile Hydrocarbon Oil or Non-Volatile Silicone Oil

Cosmetics according to the present disclosure may further contain (E) a non-volatile hydrocarbon oil or a non-volatile silicone oil.

The non-volatile hydrocarbon oil means hydrocarbon oil having a boiling point of 300° C. or higher at 1 atmosphere, which is exemplified by α-olefin oligomer, squalane, hydrogenated polydecene, and vaseline. The non-volatile silicone oil is a dimethicone that does not volatilize at room temperature under ordinary pressure, and silicone oils having a viscosity of 5 cs to 100 cs, preferably a viscosity of 10 cs, 6 cs, or 5 cs are selected.

As (E) ingredient, each of a non-volatile hydrocarbon oil and a non-volatile silicone oil may be used alone, or both may be used simultaneously. The mix proportion of (E) ingredient is, relative to the entire amount of a cosmetic, preferably 10% by weight or less, more preferably 7% by weight or less, and more preferably 5% by weight or less. When the mix proportion of (E) ingredient is 10% by weight or less, greasiness can be further suppressed.

The ratio of (E) ingredient to (B) ingredient ((E) ingredient/(B) ingredient) is preferably 0.5 or lower, more preferably 0.4 or lower, and still more preferably 0.2 or lower. In cases where (E) ingredient is contained, when the ratio of (E) ingredient/(B) ingredient is 0.5 or lower, a stronger smooth feel derived from a starch powder is perceptible.

In addition to the above ingredients, one or more types of ingredients that are ordinarily used in cosmetics and quasi-drugs, such as moisturizers, powder ingredients, liquid fats and oils, solid fats and oils, waxes, higher alcohols, surfactants, thickeners (excluding (D) ingredient), and saccharides may be mixed with cosmetics according to the present disclosure. Examples of mixable ingredients are described below.

Examples of the moisturizers include polyethylene glycol, propylene glycol, glycerin, 1,3-butylene glycol, xylitol, sorbitol, maltitol, chondroitin sulfate, hyaluronic acid, mucoitin sulfuric acid, caronic acid, atelocollagen, sodium lactate, bile salts, DL-pyrrolidone carboxylate, short chain soluble collagen, diglycerin (EO) PO adduct, *Rosa Roxburghii* Fruit extract, *Achillea millefolium* extract, and Merrilot extract.

Examples of the powder ingredients include inorganic powders (such as talc, kaolin, mica, sericite, white mica, phlogopite, synthetic mica, lepidolite, biotite, vermiculite, magnesium carbonate, calcium carbonate, aluminum silicate, barium silicate, calcium silicate, magnesium silicate, strontium silicate, metal tungstate, magnesium, silica, zeolite, barium sulfate, calcined calcium sulfate (calcined gypsum), calcium phosphate, fluoroapatite, hydroxyapatite, ceramic powder, metal soaps (such as zinc myristate, calcium palmitate, and aluminum stearate), and boron nitride); organic powders (such as a polyamide resin powder (nylon powder), a polyethylene powder, a methyl polymethacrylate powder, a polystyrene powder, a styrene/acrylic acid copolymer resin powder, a benzoguanamine resin powder, a polytetrafluoroethylene powder, and a cellulose powder); inorganic white pigments (such as zinc oxide); inorganic red pigments (such as iron titanate); inorganic violet pigments (such as mango violet and cobalt violet); inorganic green pigments (such as chromium oxide, chromium hydroxide, and cobalt titanate); inorganic blue pigments (such as ultramarine blue and iron blue); pearl pigments (such as titanium oxide-coated mica, titanium oxide-coated bismuth oxychloride, titanium oxide-coated talc, colored titanium oxide-coated mica, bismuth oxychloride, and fish scale flake); metal powder pigments (such as aluminum powder and copper powder); organic pigments of zirconium, barium, and aluminum lakes (such as organic pigments including Red No. 201, Red No. 202, Red No. 204, Red No. 205, Red No. 220, Red No. 226, Red No. 228, Red No. 405, Orange No. 203, Orange No. 204, Yellow No. 205, Yellow No. 401, and Blue No. 404, Red No. 3, Red No. 104, Red No. 106, Red No. 227, Red No. 230, Red No. 401, Red No. 505, Orange No. 205, Yellow No. 4, Yellow No. 5, Yellow No. 202, Yellow No. 203, Green No. 3, and Blue No. 1); and natural dyes (such as chlorophyll and β-carotin).

Examples of the liquid fats and oils include avocado oil, *camellia* oil, turtle oil, macadamia nut oil, maize oil, mink oil, olive oil, rapeseed oil, egg-yolk oil, sesame oil, persic oil, wheat germ oil, *Camellia sinensis* leaf oil, castor oil, linseed oil, safflower oil, cotton seed oil, perilla oil, soybean oil, peanut oil, tea seed oil, kaya oil, rice bran oil, tung oil, Japanese tung oil, jojoba oil, germ oil, and triglycerin.

Examples of the solid fats and oils include cacao butter, coconut oil, horse fat, hardened coconut oil, palm oil, beef tallow, mutton tallow, hardened beef tallow, palm kernel oil, lard, beef bone fat, Japan tallow kernel oil, hardened oil, neat's foot oil, Japan tallow, and hydrogenated castor oil.

Examples of the waxes include beeswax, candelilla wax, cotton wax, carnauba wax, bayberry wax, insects wax, spermaceti, montan wax, bran wax, lanoline, kapok wax, acetylated lanoline, liquid lanoline, sugarcane wax, lanolin fatty acid isopropyl ester, hexyl laurate, reduced lanoline, jojoba wax, hardened lanoline, shellac wax, POE lanoline alcohol ether, POE lanoline alcohol acetate, POE cholesterol ether, lanolin fatty acid polyethylene glycol, and POE hydrogenated lanoline alcohol ether.

Examples of the higher fatty acids include lauric acid, myristic acid, palmitic acid, stearic acid, behenic acid, oleic acid, undecylenic acid, tall oil acid, isostearic acid, linolic acid, linoleic acid, eicosapentaenoic acid (EPA), and docosahexaenoic acid (DHA).

Examples of the higher alcohols include linear alcohols (such as lauryl alcohol, cetyl alcohol, stearyl alcohol, behenyl alcohol, myristyl alcohol, oleyl alcohol, and cetostearyl alcohol); and branched alcohols (such as monostearyl glycerin ether (batyl alcohol), 2-decyltetradecynol, lanolin alcohol, cholesterol, phytosterol, hexyl dodecanol, isostearyl alcohol, and octyl dodecanol).

In addition, various types of surfactants may be mixed with cosmetics according to the present disclosure as emulsifiers.

Examples of anionic surfactants include fatty acid soaps (such as sodium laurate and sodium palmitate); higher alkyl sulfate salts (such as sodium lauryl sulfate and potassium lauryl sulfate); alkyl ether sulfate salts (such as triethanolamine POE-lauryl sulfate and sodium POE-lauryl sulfate); N-acylsarcosinic acids (such as sodium lauroylsarcosinate); higher fatty acid amide sulfonate salts (such as sodium N-methyl-N-myristoyl taurate, sodium coconut oil fatty acid methyl tauride, and sodium lauryl methyl tauride); phosphate salts (such as sodium POE-oleyl ether phosphate and POE-stearyl ether phosphate); sulfosuccinates (such as sodium di-2-ethylhexylsulfosuccinate, sodium monolauroylmonoethanolamide polyoxyethylene sulfosuccinate, and sodium laurylpolypropylene glycol sulfosuccinate); alkylbenzenesulfonates (such as sodium linear dodecylbenzenesulfonate, triethanolamine linear dodecylbenzenesulfonate, and linear dodecylbenzenesulfonic acid); higher fatty acid ester sulfate salts (such as sodium hydrogenated coconut oil fatty acid glycerin sulfate); N-acylglutamate salts (such as monosodium N-lauroylglutamate, disodium N-stearoylglutamate, and monosodium N-myristoyl-L-glutamate); sulfonated oil (such as Turkey red oil); POE-alkyl ether carboxylic acids; POE-alkylallyl ether carboxylate salts; α-olefin sulfonate salts; higher fatty acid ester sulfonate salts; secondary alcohol sulfate salts; higher fatty acid alkylolamide sulfate salts; sodium lauroyl monoethanolamide succinate; ditriethanolamine N-palmitoylaspartate; and casein sodium.

Examples of cationic surfactants include alkyl trimethyl ammonium salts (such as stearyl trimethyl ammonium chloride and lauryl trimethyl ammonium chloride); alkylpyridinium salts (such as cetylpyridinium chloride); distearyl dimethyl ammonium chloride dialkyl dimethyl ammonium salts; poly (N,N'-dimethyl-3,5-methylene piperidinium)

chloride; alkyl quaternary ammonium salts; alkyl dimethyl benzyl ammonium salts; alkyl isoquinolinium salts; dialkyl morpholinium salts; POE-alkylamines; alkylamine salts; polyamine fatty acid derivatives; amyl alcohol fatty acid derivatives; benzalkonium chloride; and benzethonium chloride.

Examples of amphoteric surfactants include imidazoline-based amphoteric surfactants (such as sodium 2-undecyl-N,N,N-(hydroxyethylcarboxymethyl)-2-imidazolate and 2-cocoyl-2-imidazoliniumhydroxide-1-carboxyethyloxy disodium salts); and betaine-based surfactants (such as 2-heptadecyl-N-carboxymethyl-N-hydroxyethylimidazolinium betaine, betaine lauryldimethylaminoacetate, alkylbetaine, amidebetaine, and sulfobetaine).

Examples of lipophilic nonionic surfactants include sorbitan fatty acid esters (such as sorbitan monooleate, sorbitan monoisostearate, sorbitan monolaurate, sorbitan monopalmitate, sorbitan monostearate, sorbitan sesquioleate, sorbitan trioleate, penta-2-ethylhexylic acid diglycerolsorbitan, and tetra-2-ethylhexylic acid diglycerolsorbitan); glycerin polyglycerin fatty acid esters (such as cotton seed oil fatty acid monoglycerin, glycerin monoerucate, glycerin sesquioleate, glycerin monostearate, glycerin α,α'-oleic acid pyroglutamate, and glycerin monostearate malate); propylene glycol fatty acid esters (such as propylene glycol monostearate); hydrogenated castor oil derivatives; and glycerin alkyl ether.

Examples of hydrophilic nonionic surfactants include POE-sorbitan fatty acid esters (such as POE-sorbitan monooleate, POE-sorbitan monostearate, and POE-sorbitan tetraoleate); POE-sorbitol fatty acid esters (such as POE-sorbitol monolaurate, POE-sorbitol monooleate, POE-sorbitol pentaoleate, and POE-sorbitol monostearate); POE-glycerin fatty acid esters (such as POE-monooleates including POE-glycerin monostearate, POE-glycerin monoisostearate, and POE-glycerin triisostearate); POE-fatty acid esters (such as POE-distearate, POE-monodioleate, and ethylene glycol distearate); POE-alkyl ethers (such as POE-lauryl ether, POE-oleyl ether, POE-stearyl ether, POE-behenyl ether, POE-2-octyl dodecyl ether, and POE-cholestanol ether); Pluronic types (such as Pluronic); POE·POP-alkyl ethers (such as POE·POP-cetyl ether, POE·POP-2-decyl tetradecyl ether, POE·POP-monobutyl ether, POE·POP-hydrogenated lanolin, and POE·POP-glycerin ether); tetra-POE/tetra-POP-ethylenediamine condensates (such as Tetronic); POE-castor oil hydrogenated castor oil derivatives (such as POE-castor oil, POE-hydrogenated castor oil, POE-hydrogenated castor oil monoisostearate, POE-hydrogenated castor oil triisostearate, POE-hydrogenated castor oil monopyroglutamic acid monoisostearic acid diester, and POE-hydrogenated castor oil maleic acid); POE-beeswax/lanolin derivatives (such as POE-sorbitol beeswax); alkanolamide (such as coconut oil fatty acid diethanolamide, lauric acid monoethanolamide, and fatty acid isopropanolamide); POE-propylene glycol fatty acid esters; POE-alkylamines; POE-fatty acid amides; sucrose fatty acid esters; alkyl ethoxy dimethylamine oxides; and trioleyl phosphoric acid.

As the thickener, thickeners other than (D) ingredient may also be mixed in. Specific examples include vegetable-based polymers such as gum arabic, tragacanth gum, galactan, carob gum, guar gam, karaya gum, carageenan, xanthan gum, pectin, agar, quince seed (marmelo), and algecolloid (phaeophyta extract), microbe-based polymers such as dextran, succinoglycan, and pullulan; animal-based polymers such as collagen, casein, albumin, and gelatin; cellulose-based polymers such as methylcellulose, nitrocellulose, ethyl cellulose, methylhydroxypropyl cellulose, hydroxyethyl cellulose, sodium cellulose sulfate, hydroxypropyl cellulose, sodium carboxymethyl cellulose, crystalline cellulose, and cellulose powder; alginic acid-based polymers such as sodium alginate, and propyleneglycol alginate.

Additional examples include vinyl-based polymers such as polyvinylmethyl ether and carboxyvinyl polymer, polyoxyethylene-based polymers, polyoxyethylene polyoxypropylene copolymer-based polymers, acryl-based polymers such as polyethylacrylate and polyacrylamide, polyethylene imine, cationic polymers, water-soluble inorganic polymers for example of bentonite, aluminum magnesium silicate, laponite, hectorite, and silicic anhydride, copolymers such as PEG-240/decyltetradeces-20/hexamethylene diisocyanate copolymer, (dimethylacrylamide/acryloyldimethyl taurine Na) cross polymer, (acrylic acid Na/acryloyldimethyl taurine) copolymer, (alkyl acrylate/steareth-20 methacrylate) copolymer, and (acryloyldimethyl taurine ammonium/VP) copolymer, and materials such as dextrin, sodium pectinate, sodium alginate, dialkyl dimethyl ammonium sulfate cellulose, aluminum magnesium silicate, bentonite, hectorite, AlMg silicate (Veegum), laponite, and silicic anhydride.

Examples of the monosaccharides include trioses (such as D-glyceryl aldehyde and dihydorxyacetone); tetroses (such as D-erythrose, D-erythrulose, and D-treose); pentoses (such as L-arabinose, D-xylose, L-lyxose, D-arabinose, D-ribose, D-ribulose, D-xylulose, and L-xylulose); hexoses (such as D-glucose, D-talose, D-psicose, D-galactose, D-fructose, L-galactose, L-mannose, and D-tagatose); heptoses (such as aldoheptose and heplose); octoses (such as octulose); deoxy sugars (such as 2-deoxy-D-ribose, 6-deoxy-L-galactose, and 6-deoxy-L-mannose); amino sugars (such as D-glucosamine, D-galactosamine, sialic acids, amino uronic acids, and muramic acid); and uronic acids (such as D-glucuronic acid, D-mannuronic acid, L-guluronic acid, D-galacturonic acid, and L-iduronic acid).

Examples of oligosaccharides include sucrose, gentianose, umbelliferose, lactose, planteose, and isolychnoses, α,α-trehalose, raffinose, lychnoses, umbillicin, and stachyose verbascoses.

Examples of amino acids include neutral amino acids (such as threonine and cysteine); and basic amino acids (such as hydroxylysine). Examples of amino acid derivatives include sodium acyl sarcosinate (sodium lauroyl sarcosinate), acyl glutamate, sodium acyl β-alanine, glutathione, and pyrrolidone carboxylic acid.

Examples of organic amines include monoethanolamine, diethanolamine, triethanolamine, morpholine, triisopropanolamine, 2-amino-2-methyl-1,3-propanediol, and 2-amino-2-methyl-1-propanol.

Examples of alkylene oxide derivatives include POE(9)/POP(2) dimethyl ether, POE(14)/POP(7) dimethyl ether, POE(10)/POP(10) dimethyl ether, POE(6)/POP(14) dimethyl ether, POE(15)/POP(5) dimethyl ether, POE(25)/POP(25) dimethyl ether, POE(7)/POP(12) dimethyl ether, POE(22)/POP(40) dimethyl ether, POE(35)/POP(40) dimethyl ether, POE(50)/POP(40) dimethyl ether, POE(55)/POP(30) dimethyl ether, POE(30)/POP(34) dimethyl ether, POE(25)/POP(30) dimethyl ether, POE(27)/POP(14) dimethyl ether, POE(55)/POP(28) dimethyl ether, POE(36)/POP(41) dimethyl ether, POE(7)/POP(12) dimethyl ether, and POE(17)/POP(4) dimethyl ether.

Examples of sequestering agents include 1-hydroxyethane-1,1-diphosphonic acid, 1-hydroxyethane-1,1-diphosphonic acid tetrasodium salt, disodium edetate, trisodium edetate, tetrasodium edetate, sodium citrate, sodium polyphosphate, sodium metaphosphate, gluconic acid, phosphoric acid, citric acid, ascorbic acid, succinic acid, edetic acid, and trisodium ethylenediamine hydroxyethyl triacetate.

Examples of antioxidant auxiliaries include phosphoric acid, citric acid, ascorbic acid, maleic acid, malonic acid, succinic acid, fumaric acid, kephalin, hexametaphosphate, phytic acid, and ethylene diamine tetraacetic acid.

Examples of other ingredients which can be mixed in include preservatives (such as ethylparaben and butylparaben); whitening agents (such as placenta extract, *Saxifraga sarmentosa* extract, and arbutin); blood circulation promoters (such as nicotinic acid, benzyl nicotinate, tocopherol nicotinate, nicotinic acid β-butoxy ester, minoxidil or analogues thereof, γ-orizanol, alkoxycarbonylpyridine N-oxide, carpronium chloride, and acetylcholine or derivatives thereof); extracts (for example extracts from ginger, phellodendron bark, coptis root, lithospermi radix, birch, loquat, carrot, aloe, mallow, iris, grape, loofah, lily, saffron, cnidium rhizome, *Zingiber officinale, hypericum, Ononis spinosa,* garlic, *capsicum,* citrus unshiu peel, *Angelica acutiloba, Paeonia suffruticosa,* and seaweeds), activators (such as panthenyl ethyl ether, amide nicotinate, biotin, pantothenic acid, royal jelly, and cholesterol derivatives); and antiseborrheic agents (such as pyridoxines and thianthol).

Cosmetics according to the present disclosure may have any form and can be provided in any forms such as an emulsified form or a water/oil two layer-based form.

Cosmetics according to the present disclosure may be used as they are or may be used as oily cosmetics by diluting them with oily ingredients. In addition, cosmetics according to the present disclosure may be used as water-in-oil emulsified cosmetics by emulsifying the cosmetics with aqueous ingredients by publicly known methods.

When aqueous ingredients are used, those ordinarily mixable in cosmetics may be used as long as the stability of cosmetics is not lost.

Examples of such aqueous ingredients include water, lower alcohols, moisturizers, water-soluble thickeners, water-soluble UV absorbers, sequestering agents, antioxidants, and water-soluble drugs.

Product forms of cosmetics according to the present disclosure are not particularly limited and any product forms may be broadly employed as long as they are employed for conventional cosmetics including basic cosmetic products such as lotions, milky lotions, creams, facial cleansers, gels, essences (serums), and facial packs; makeup products such as lipsticks, eye shadows, eyeliners, mascaras, foundations, and sunscreens, oral cosmetic products, fragrant cosmetic products, hair cosmetic products, and body cosmetic products.

EXAMPLES

The present disclosure is more closely described below with reference to, but not limited to, examples. In the examples below, mix proportions are represented by % by weight unless otherwise referred to.

Water-in-oil emulsified cosmetics having compositions shown in Tables 1 to 3 below were prepared by an ordinary method in which a powder for adjusting usability is dispersed in an oil phase.

The afterfeel of the obtained cosmetics were evaluated in accordance with the following criteria.
(Smooth Feel)

Five female special panelists actually applied the cosmetics on their skin and evaluated the smooth feel of the cosmetics.

A: Five panelists found a smooth feel.
B: Four panelists found a smooth feel.
C: Three panelists found a smooth feel.
D: Two or less panelists found a smooth feel.
The evaluation results and formulations are summarized in Tables 1 to 3.

TABLE 1

| Groups | | Ingredient name | Example 1 | Comparative Example 1 | Comparative Example 2 | Comparative Example 3 |
|---|---|---|---|---|---|---|
| Oil phase | Volatile oil | Isododecane | 5 | 5 | 5 | 5 |
| | | Dimethicone (1.5 cs) | 10 | 10 | 10 | 10 |
| | | Cyclomethicone | 5 | 5 | 5 | 5 |
| | Polar oil | Isopropyl myristate | 3 | 3 | 3 | 3 |
| | UV absorber | Ethylhexyl methoxycinnamate | 11 | 11 | 11 | 11 |
| | | Octocrylene | 3 | 3 | 3 | 3 |
| | | Polysilicone-15 | 2 | 2 | 2 | 2 |
| | | Bis-ethylhexyloxyphenol methoxyphenyl triazine | 0.5 | 0.5 | 0.5 | 0.5 |
| | | Diethyl amino hydroxybenzoyl hexyl benzoate | 1 | 1 | 1 | 1 |
| | | Ethylhexyl salicylate | 3 | 3 | 3 | 3 |
| | | Homosalate | 2 | 2 | 2 | 2 |
| | Non-volatile silicone oil | Dimethicone (6 cs) | 1 | 1 | 1 | 1 |
| | Surfactant | PEG-9 polydimethysiloxyethyl dimethicone | 1.5 | 1.5 | 1.5 | 1.5 |
| | Oil phase thickener | Dimethyldistearylammonium hectorite | 0.3 | 0.3 | 0.3 | 0.3 |
| | UV scattering agent | Hydrophobized titanium oxide | 1 | 1 | 1 | 1 |
| | | Hydrophobized zinc oxide | 12 | 12 | 12 | 12 |
| | Powder for adjusting usability | Cornstarch | 8 | 0 | 0 | 0 |
| | | Methyl polymethacrylate | 0 | 8 | 0 | 0 |
| | | Crosslinked silicone/net-like silicone block copolymer | 0 | 0 | 8 | 0 |
| | | Polyethylene powder | 0 | 0 | 0 | 8 |
| | | Hydrophobized talc | 5 | 5 | 5 | 5 |
| Water Phase | Water | Water | 12.55 | 12. 55 | 12 55 | 12.55 |
| | Chelating agent | Chelating agent | 0.05 | 0. 05 | 0. 05 | 0.05 |
| | Emulsion stabilizer | Salt | 0.1 | 0.1 | 0. 1 | 0.1 |
| | Alcohol | Ethanol | 8 | 8 | 8 | 8 |
| | Moisturizer | Glycerin | 3 | 3 | 3 | 3 |

TABLE 1-continued

| Groups | Ingredient name | Example 1 | Comparative Example 1 | Comparative Example 2 | Comparative Example 3 |
|---|---|---|---|---|---|
| (B) Polar oil | | 25.5 | 25.5 | 25.5 | 25.5 |
| (C) Volatile oil | | 20 | 20 | 20 | 20 |
| (E) Non-volatile hydrocarbon oil or silicone oil | | 1 | 1 | 1 | 1 |
| (C) Ingredient/(B) ingredient (0.5 or higher) | | 0.78 | 0.78 | 0.78 | 0.78 |
| (E) Ingredient/(B) Ingredient (0.5 or lower) | | 0.04 | 0.04 | 0.04 | 0.04 |
| Smooth feel | | A | D | D | D |

TABLE 2

| Groups | | Ingredient name | Comparative Example 4 | Comparative Example 5 | Comparative Example 6 | Example 2 | Example 3 |
|---|---|---|---|---|---|---|---|
| Oil phase | Volatile oil | Isododecane | 0 | 5 | 10 | 15 | 20 |
| | Polar oil | Isopropyl myristate | 3 | 3 | 3 | 3 | 3 |
| | UV absorber | Ethylhexyl methoxycinnamate | 30 | 25 | 20 | 15 | 10 |
| | | Octocrylene | 3 | 3 | 3 | 3 | 3 |
| | | Polysilicone-15 | 2 | 2 | 2 | 2 | 2 |
| | | Bis-ethylhexyloxyphenol methoxyphenyl triazine | 0.5 | 0.5 | 0.5 | 0.5 | 0.5 |
| | | Diethylamino hydroxybenzoyl hexyl benzoate | 1 | 1 | 1 | I | 1 |
| | | Ethylhexyl salicylate | 3 | 3 | 3 | 3 | 3 |
| | | Homosalate | 2 | 2 | 2 | 2 | 2 |
| | Non-volatile silicone oil | Dimethicone (6 cs) | 4 | 4 | 4 | 4 | 4 |
| | Surfactant | PEG-9 polydimethylsiloxyethyl dimethicone | 1.5 | 1.5 | 1.5 | 1.5 | 1.5 |
| | Oil phase thickener | Dimethyldistearyl ammonium hectorite | 0.3 | 0.3 | 0.3 | 0.3 | 0.3 |
| | UV scattering agent | Hydrophobized titanium oxide | 1 | 1 | 1 | I | 1 |
| | | Hydrophobized zinc oxide | 12 | 12 | 12 | 12 | 12 |
| | Powder for adjusting usability | Cornstarch | 8 | 8 | 8 | 8 | 8 |
| | | Hydrophobized talc | 5 | 5 | 5 | 5 | 5 |
| | | Silicic anhydride | 2 | 2 | 2 | 2 | 2 |
| Water Phase | Water | Water | 12.55 | 12.55 | 12.55 | 12.55 | 12.55 |
| | Chelating agent | Chelating agent | 0.05 | 0.05 | 0.05 | 0.05 | 0.05 |
| | Emulsion stabilizer | Salt | 0.1 | 0.1 | 0.1 | 0.1 | 0.1 |
| | Alcohol | Ethanol | 8 | 8 | 8 | 8 | 8 |
| | Moisturizer | Glycerin | 3 | 3 | 3 | 3 | 3 |
| (B) Polar oil | | | 44.5 | 39.5 | 34.5 | 29.5 | 24.5 |
| (C) Volatile oil | | | 0 | 5 | 10 | 15 | 20 |
| (E) Non-volatile hydrocarbon oil or silicone oil | | | 4 | 4 | 4 | 4 | 4 |
| (C) Ingredient/(B) ingredient (0.5 or higher) | | | 0.00 | 0.13 | 0.29 | 0.51 | 0.82 |
| (E) Ingredient/(B) Ingredient (0.5 or lower) | | | 0.09 | 0.10 | 0.12 | 0.14 | 0.16 |
| Smooth feel | | | D | D | D | B | A |

45

TABLE 3

| Groups | | Ingredient name | Example 4 | Example 5 | Example 6 | Example 7 | Example 8 | Example 9 |
|---|---|---|---|---|---|---|---|---|
| Oil phase | Volatile oil | Isododecane | 5 | 5 | 5 | 5 | 5 | 5 |
| | | Dimethicone (1.5 cs) | 10 | 10 | 10 | 10 | 10 | 10 |
| | | Cyclomethicone | 5 | 5 | 5 | 5 | 5 | 5 |
| | Polar oil | Isopropyl myristate | 3 | 3 | 3 | 3 | 3 | 3 |
| | UV absorber | Ethylhexyl methoxycinnamate | 11 | 7 | 3 | 11 | 7 | 3 |
| | | Octocrylene | 3 | 3 | 3 | 3 | 3 | 3 |
| | | Polysilicone-15 | 2 | 2 | 2 | 2 | 2 | 2 |
| | | Bis-ethylhexyloxyphenol methoxyphenyl triazine | 0.5 | 0.5 | 0.5 | 0.5 | 0.5 | 0.5 |
| | | Diethylaminohydroxybenzoyl hexyl benzoate | 1 | 1 | 1 | I | 1 | 1 |
| | | Ethylhexyl salicylate | 3 | 3 | 3 | 3 | 3 | 3 |
| | | Homosalate | 2 | 2 | 2 | 2 | 2 | 2 |

TABLE 3-continued

| Groups | | Ingredient name | Example 4 | Example 5 | Example 6 | Example 7 | Example 8 | Example 9 |
|---|---|---|---|---|---|---|---|---|
| | Non-volatile silicone oil | Dimethicone (6 cs) | 1 | 5 | 9 | 0 | 0 | 0 |
| | Non-volatile hydrocarbn oil | α-olefin oligomer | 0 | 0 | 0 | 1 | 5 | 9 |
| | Surfactant | PEG-9 polydimethylsiloxyethyl dimethicone | 1.5 | 1.5 | 1.5 | 1.5 | 1.5 | 1.5 |
| | Oil phase thickener | Dimethyldistearyl ammonium hectorite | 0.3 | 0.3 | 0.3 | 0.3 | 0.3 | 0.3 |
| | UV scattering agent | Hydrophobized titanium oxide | 1 | 1 | 1 | I | 1 | 1 |
| | | Hydrophobized zinc oxide | 12 | 12 | 12 | 12 | 12 | 12 |
| | Powder for adjusting usability | Cornstarch | 8 | 8 | 8 | 8 | 8 | 8 |
| | | Hydrophobized talc | 5 | 5 | 5 | 5 | 5 | 5 |
| | | Silicic anhydride | 2 | 2 | 2 | 2 | 2 | 2 |
| Water Phase | Water | Water | 12.55 | 12.55 | 12.55 | 12.55 | 12.55 | 12.55 |
| | Chelating agent | Chelating agent | 0.05 | 0.05 | 0.05 | 0.05 | 0.05 | 0.05 |
| | Emulsion stabilizer | Salt | 0.1 | 0.1 | 0.1 | 0.1 | 0.1 | 0.1 |
| | Alcohol | Ethanol | 8 | 8 | 8 | 8 | 8 | 8 |
| | Moisturizer | Glycerin | 3 | 3 | 3 | 3 | 3 | 3 |
| (B) Polar oil | | | 25.5 | 21.5 | 17.5 | 25.5 | 21.5 | 17.5 |
| (C) Volatile oil | | | 20 | 20 | 20 | 20 | 20 | 20 |
| (E) Non-volatile hydrocarbon oil or silicone oil | | | 1 | 5 | 9 | 1 | 5 | 9 |
| (C) Ingredient/(B) ingredient (0.5 or higher) | | | 0.78 | 0.93 | 1.14 | 0.78 | 0.93 | 1.14 |
| (E) Ingredient/(B) Ingredient (0.5 or lower) | | | 0.04 | 0.23 | 0.51 | 0.04 | 0.23 | 0.51 |
| Smooth feel | | | A | B | C | A | B | C |

As shown in Table 1, a prominent smooth feel was obtained with Example 1 containing a starch powder, compared with that obtained with Comparative Examples 1 to 3 containing other powders for adjusting usability. Due to the ratio of (C) ingredient/(B) ingredient being lower than 0.5, no smooth feel was obtained with Comparative Examples 4 to 6 shown in Table 2. With Examples 2 and 3, a smooth feel was obtained due to the ratio of (C) ingredient/(B) ingredient being 0.5 or higher. In addition, a comparison between Examples 4, 5, 7, and 8 and Examples 6 and 9 in Table 3 shows that a stronger smooth feel can be obtained when the ratio of (E) ingredient/(B) ingredient is 0.5 or lower.

Next, oily cosmetics having the compositions summarized in Table 4 below were prepared by an ordinary method and were evaluated in accordance with the same criteria as those described above.

As shown in Table 4, a smooth feel was difficult to obtain with Comparative Examples 7 and 8 in which the ratio of (C) ingredient/(B) ingredient was lower than 0.5. In addition, a comparison among Examples 10 to 13 shows that in the case where (E) ingredient is contained, a stronger smooth feel can be obtained when the ratio of (E) ingredient/(B) ingredient is 0.5 or lower.

FORMULATION EXAMPLES

The formulation examples of cosmetics according to the present disclosure are described below. However, the present disclosure is not limited to the formulation examples. All the mix proportions are represented by % by weight relative to the entire amounts of products.

TABLE 4

| Groups | Ingredient name | Example 10 | Example 11 | Example 12 | Example 13 | Comparative Example 7 | Comparative Example 8 |
|---|---|---|---|---|---|---|---|
| Powder for adjusting usability | Cornstarch | 10 | 10 | 10 | 10 | 10 | 10 |
| Volatile oil | Isododecane | 51 | 51 | 51 | 31 | — | — |
| | dimethicone (1.5 cs) | 10 | I0 | 10 | I0 | 10 | 10 |
| Non-volatile hydrocarbon oil | α-olefin oligomer | — | 10 | — | 10 | 31 | — |
| Non-volatile silicone oil | Dimethicone (6 cs) | — | — | 10 | — | — | — |
| Polar oil | Glyceryl tri-2-ethylhexanoate | 5 | 5 | 5 | 5 | 5 | 56 |
| | Ethylhexyl methoxycinnamate | 10 | — | — | 20 | 30 | 10 |
| | Octocrylene | 5 | 5 | 5 | 5 | 5 | 5 |
| | Homosalate | 5 | 5 | 5 | 5 | 5 | 5 |
| | Diethylamino hydroxybenzoyl hexyl benzoate | 2 | 2 | 2 | 2 | 2 | 2 |
| | Bis-ethylhexyloxyphenol methoxyphenyl triazine | 1 | 1 | 1 | 1 | 1 | 1 |
| Oil phase thickener | Dextrin palmitate | 1 | 1 | 1 | 1 | 1 | 1 |
| (B) Polar oil | | 28 | 18 | 18 | 38 | 48 | 79 |
| (C) Volatile oil | | 61 | 61 | 61 | 41 | 10 | 10 |
| (E) Non-volatile hydrocarbon oil or silicone oil | | 0 | 10 | 10 | 10 | 31 | 0 |
| (0) Ingredient/(B) Ingredient (0.5 or higher) | | 2.18 | 3.39 | 3.39 | 1.08 | 0.21 | 0.13 |
| (E) Ingredient/(8) Ingredient (0.5 or lower) | | 0.00 | 0.56 | 0.56 | 0.26 | 0.65 | 0.00 |
| Smooth feel | | A | C | C | B | D | D |

Formulation Example 1: Two-Layer Type Makeup Foundation

| Ingredient name | Mix proportion |
| --- | --- |
| Purified water | remainder |
| Ethanol | 5 |
| PEG/PPG-9/2 dimethyl ether | 1 |
| Glycerin | 1 |
| Xylitol | 1 |
| Tormentil extract | 0.3 |
| Sodium hyaluronate | 0.1 |
| 2-O-ethyl-L-ascorbic acid | 0.1 |
| Dipotassium glycyrrhizinate | 0.05 |
| Isododecane | 3 |
| Diisopropyl sebacate | 10 |
| PBG/PPG-9/1 copolymer | 1 |
| Volatile dimethicone | 12 |
| Non-volatile dimethicone | 1 |
| Caprylyl methicone | 3 |
| Dimethicone solution of 20% highly polymerized aminopropyl dimethicone | 1 |
| Dimethicone solution of 50% trifluoroalkyldimethyl/trimethylsiloxysilicate | 3 |
| Dextrin palmitate | 0.5 |
| Ethylhexyl methoxycinnamate | 7 |
| Octocrylene | 5 |
| Diethylamino hydroxybenzoyl hexyl benzoate | 1 |
| Bis-ethylhexyloxyphenol methoxyphenyl triazine | 0.5 |
| Hydrophobized titanium oxide fine particles | 2 |
| Hydrophobized zinc oxide fine particles | 5 |
| Hydrophobized pigment grade titanium oxide | 1 |
| Hydrophobized iron oxide | 0.07 |
| Methyl Methacrylate crosspolymer | 2 |
| Vinyl dimethicone/methicone silsesquioxane crosspolymer | 2 |
| Hydrophobized talc | 2 |
| Cornstarch | 5 |
| PEG-9 polydimethyl siloxyethyl dimethicone | 1.5 |
| PEG/PPG-19/19 dimethicone | 0.3 |
| Dimethyldistearylammonium hectorite | 0.4 |
| Isostearic acid | 0.3 |
| EDTA•3Na | proper amount |
| Salt | proper amount |
| Sodium metabisulfite | proper amount |
| Tocopherol | proper amount |
| Perfume | proper amount |

Formulation Example 2: Cream Type Foundation

| Ingredient name | Mix proportion |
| --- | --- |
| Purified water | Remainder |
| Ethanol | 5 |
| Phenoxyethanol | 1 |
| PEG/PPG-9/2 dimethyl ether | 0.5 |
| Glycerin | 3 |
| Erythritol | 1 |
| Xylitol | 1 |
| Tormentil extract | 1 |
| Glycyl glycine | 0.1 |
| Tranexamic acid | 1 |
| Dipotassium glycyrrhizinate | 0.05 |
| Tripropylene glycol pivalate | 2 |
| Diisopropyl sebacate | 5 |
| Volatile dimethicone | 10 |
| Cyclomethicone | 5 |
| Cyclopentasiloxane solution of 50% trisiloxysilicate | 2 |
| Dextrin palmitate | 1 |
| Ethylhexyl methoxycinnamate | 7 |
| Hydrophobized titanium oxide fine particles | 3 |
| Hydrophobized zinc oxide fine particles | 3 |
| Hydrophobized pigment grade titanium oxide | 6 |
| Hydrophobized iron oxide | 3.2 |
| Hydrophobized barium sulfate-coated titanium mica | 0.01 |
| Hydrophobized titanium mica | 0.01 |
| Cyclopentasiloxane mixture containing 13% dimethicone crosspolymer | 2 |
| Polymethyl silsesquioxane | 2 |
| Methylmethacrylate crosspolymer | 2 |
| Cornstarch | 2 |
| Hydrophobized silica fine particles | 0.5 |
| Lauryl PEG-9 polydimethyl siloxyethyl dimethicone | 2 |
| Dimethicone/PEG-10/15 crosspolymer | 1 |
| Dimethyldistearylammonium hectorite | 1 |
| Isostearic acid | 0.2 |
| Tocopherol | proper amount |
| EDTA•3Na | proper amount |
| Salt | proper amount |
| Sodium metabisulfite | proper amount |
| Perfume | proper amount |

Formulation Example 3: Aerosol Spray Sunscreen

| Ingredient name | Mix proportion |
| --- | --- |
| Purified water | Remainder |
| Ethanol | 5 |
| Polyethylene glycol 300 | 2 |
| Silica | 0.5 |
| Glycerin | 1 |
| PEG/PPG-14/7-dimethyl ether | 6 |
| DL-α-tocopherol acetate | 0.5 |
| D-glutamic acid | 0.1 |
| Stearyl glycyrrhetinate | 0.1 |
| Isododecane | 10 |
| Glycerol tris(2-ethylhexanoate) | 5 |
| Isopropyl myristate | 3 |
| Diisopropyl sebacate | 5 |
| Hydrogenated polydecene | 3 |
| PBG/PPG-9/1 copolymer | 1 |
| Volatile dimethicone | 10 |
| Cyclopentasiloxane solution of 50% trisiloxysilicate | 0.5 |
| Sucrose tetrastearate triacetate | 0.5 |
| Dextrin palmitate | 1 |
| Ethylhexyl methoxycinnamate | 5 |
| Diethylamino hydroxybenzoyl hexyl benzoate | 2 |
| Bis-ethylhexyloxyphenol methoxyphenyl triazine | 1 |
| Polysilicone-15 | 2 |
| Octocrylene | 5 |
| Methylmethacrylate crosspolymer | 5 |
| Vinyldimethicone/methicone silsesquioxane crosspolymer | 3 |
| Hydrophobized talc | 1 |
| Cornstarch | 1 |
| Cetyl PEG/PPG-10/1 dimethicone | 1 |
| Lauryl PEG-9 polydimethyl siloxyethyl dimethicone | 1 |
| Dimethyldistearylammonium hectorite | 0.5 |
| Isostearic acid | 0.3 |
| Sorbitan sesquiisostearate | 0.3 |
| EDTA•3Na | proper amount |
| Tocopherol | proper amount |
| Perfume | proper amount |

The above stock solution in an amount of 50% by weight was mixed with 50% by weight of LP gas and was aerosolized to produce a spray sunscreen.

The invention claimed is:

1. A cosmetic comprising
   (A) a starch powder, and
   as oils,
   (B) a polar oil, and
   (C) a volatile oil,
   wherein the cosmetic contains (E) a non-volatile hydrocarbon oil or a non-volatile silicone oil,
   wherein the mix proportion of (A) the starch powder is 0.1 to 10% by weight relative to the total amount of the cosmetic,
   wherein the mix proportion of (B) the polar oil is 5 to 30% by weight relative to the total amount of the cosmetic,
   wherein the mix proportion of (C) the volatile oil is 5 to 60% by weight relative to the total amount of the cosmetic,
   wherein the mix proportion of (E) the non-volatile hydrocarbon oil or the non-volatile silicone oil is 7% by weight or less relative to the total amount of the cosmetic, and
   wherein the ratio of (C) the volatile oil to (B) the polar oil is 0.5 or higher.

2. The cosmetic according to claim 1, wherein (A) the starch powder is dispersed in the oils.

3. The cosmetic according to claim 2, further comprising (D) an oil phase thickener.

4. The cosmetic according to claim 3 wherein the ratio of (E) the non-volatile hydrocarbon oil or the non-volatile silicone oil to (B) the polar oil is 0.5 or lower.

5. The cosmetic according to claim 2, wherein (B) the polar oil comprises a UV absorber.

6. The cosmetic according to claim 2, wherein the cosmetic is a water-in-oil type emulsified cosmetic.

7. The cosmetic according to claim 2, wherein the cosmetic is an oily cosmetic.

8. The cosmetic according to claim 1, further comprising (D) an oil phase thickener.

9. The cosmetic according to claim 8 wherein the ratio of (E) the non-volatile hydrocarbon oil or the non-volatile silicone oil to (B) the polar oil is 0.5 or lower.

10. The cosmetic according to claim 1, wherein (B) the polar oil comprises a UV absorber.

11. The cosmetic according to claim 1, wherein the cosmetic is a water-in-oil type emulsified cosmetic.

12. The cosmetic according to claim 1, wherein the cosmetic is an oily cosmetic.

* * * * *